US007295300B1

United States Patent
Bechtler et al.

(10) Patent No.: US 7,295,300 B1
(45) Date of Patent: Nov. 13, 2007

(54) DETECTING SURFACE PITS

(75) Inventors: Laurie Bechtler, Mountain View, CA (US); Vamsi Velidandla, Hayward, CA (US); Steven W. Meeks, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 185 days.

(21) Appl. No.: 11/237,257

(22) Filed: Sep. 28, 2005

(51) Int. Cl.
*G01N 21/00* (2006.01)

(52) U.S. Cl. ............................... 356/237.2; 356/237.4; 356/237.5

(58) Field of Classification Search .. 356/237.1–237.6, 356/445–448, 335–343, 364–370, 394, 398, 356/239.8, 73; 438/57–59, 73; 250/237 G, 250/559.16, 559.01, 559.09
See application file for complete search history.

(56) References Cited

U.S. PATENT DOCUMENTS

| | | | |
|---|---|---|---|
| 4,585,348 A | 4/1986 | Chastang |
| 4,870,631 A | 9/1989 | Stoddard |
| 4,873,430 A | 10/1989 | Juliana |
| 5,189,481 A | 2/1993 | Jann |
| 5,270,794 A | 12/1993 | Tsuji |
| 5,392,116 A | 2/1995 | Makosch |
| 5,416,594 A | 5/1995 | Gross |
| 5,610,897 A | 3/1997 | Yamamoto |
| 5,633,747 A | 5/1997 | Nikoonahad |
| 5,644,562 A | 7/1997 | de Groot |
| 5,798,829 A | 8/1998 | Vurens |
| 5,864,394 A | 1/1999 | Jordan |
| 5,880,838 A | 3/1999 | Marx |
| 5,903,342 A | 5/1999 | Yatsugake |
| 5,985,680 A | 11/1999 | Singhal |
| 5,986,763 A | 11/1999 | Inoue |
| 5,995,226 A | 11/1999 | Abe |
| 6,031,615 A | 2/2000 | Meeks |
| 6,081,325 A | 6/2000 | Leslie |
| 6,118,525 A | 9/2000 | Fossey |
| 6,130,749 A | 10/2000 | Meeks |
| 6,169,601 B1 | 1/2001 | Eremin |
| 6,198,533 B1 | 3/2001 | Meeks |
| 6,229,610 B1 | 5/2001 | Meeks |
| 6,268,919 B1 | 7/2001 | Meeks |
| 6,327,025 B1 * | 12/2001 | Imai ............................. 355/53 |
| 6,392,749 B1 | 5/2002 | Meeks |
| 6,624,884 B1 | 9/2003 | Imaino |
| 6,665,078 B1 | 12/2003 | Meeks |
| 6,687,008 B1 | 2/2004 | Peale |

(Continued)

*Primary Examiner*—Gregory J. Toatley, Jr.
*Assistant Examiner*—Tri Ton
(74) *Attorney, Agent, or Firm*—Caven & Aghevli LLC

(57) ABSTRACT

A system to detect pits in a surface comprises first and second radiation targeting assemblies to target a second radiation beam onto a surface, a first radiation collecting assembly that collects radiation scattered from the surface, a processor coupled to the first radiation collecting assembly, a memory module coupled to the processor and comprising logic instructions which, when executed by the processor, configure the processor to generate a first signal from radiation scattered from the first radiation beam, generate a second signal from radiation scattered from the second radiation beam, record the first signal and the second signal at an array of different positions on the surface, calculate a median value for the first signal and the second signal over the array of different positions on the surface, and use the first signal, the second signal, and the median value to detect pits in the surface.

20 Claims, 4 Drawing Sheets

U.S. PATENT DOCUMENTS

| | | |
|---|---|---|
| 6,704,435 B1 | 3/2004 | Imaino |
| 6,717,671 B1 | 4/2004 | Meeks |
| 6,751,044 B1 | 6/2004 | Meeks |
| 6,757,056 B1 | 6/2004 | Meeks |
| 6,781,103 B1 | 8/2004 | Lane |
| 2002/0015146 A1 | 2/2002 | Meeks |
| 2002/0145740 A1 | 10/2002 | Meeks |
| 2002/0163634 A1 | 11/2002 | Meeks |
| 2003/0025905 A1 | 2/2003 | Meeks |
| 2004/0017561 A1 | 1/2004 | Meeks |
| 2004/0046959 A1 | 3/2004 | Meeks |
| 2004/0160604 A1 | 8/2004 | Meeks |
| 2004/0169850 A1 | 9/2004 | Meeks |
| 2004/0233419 A1 | 11/2004 | Meeks |
| 2005/0057747 A1 | 3/2005 | Meeks |

\* cited by examiner

DETECTING SURFACE PITS

BACKGROUND

The subject matter described herein relates to surface inspection techniques, and more particularly to detecting surface pits such as, for example surface pits in a semiconductor material or in the epitaxial layer which has been deposited upon a semiconductor material.

Manufacturers of light-emitting diodes (LEDs) and other types of optoelectronic integrated circuits (ICs) grow or deposit multiple epitaxial layers on transparent or non transparent substrates, including for example sapphire and silicon carbide. Small pits, e.g., on the order of 0.2 micrometers (μm) to 2 μm in diameter can cause reductions in yield and device performance.

Semiconductor substrates such as, for example, sapphire and silicon carbide may or may not have epitaxial layers deposited upon them to produce LEDs and other types of optoelectronic integrated circuits (ICs). These substrates and or their epitaxial layers may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface. Additional inspection techniques are desirable. In particular, it is desirable to inspect EPI (epitaxial) layers for defects such as scratches, pits, particles and other defects.

BRIEF DESCRIPTION OF THE DRAWINGS

The detailed description is described with reference to the accompanying figures.

SUMMARY

In one embodiment a system to detect pits in a surface comprises a first radiation targeting assembly to target a first radiation beam onto a surface, a second radiation targeting assembly to target a second radiation beam onto a surface, a first radiation collecting assembly that collects radiation scattered from the surface, a processor coupled to the first radiation collecting assembly, and a memory module coupled to the processor. The memory module comprises logic instructions which, when executed by the processor, configure the processor to generate a first signal from radiation scattered from the first radiation beam, generate a second signal from radiation scattered from the second radiation beam, record the first signal and the second signal at an array of different positions on the surface, calculate a median value for the first signal and the second signal over the array of different positions on the surface, and use the first signal, the second signal, and the median value to detect pits in the surface.

DETAILED DESCRIPTION

Described herein are exemplary systems and methods for detecting surface pits. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Figure 1:
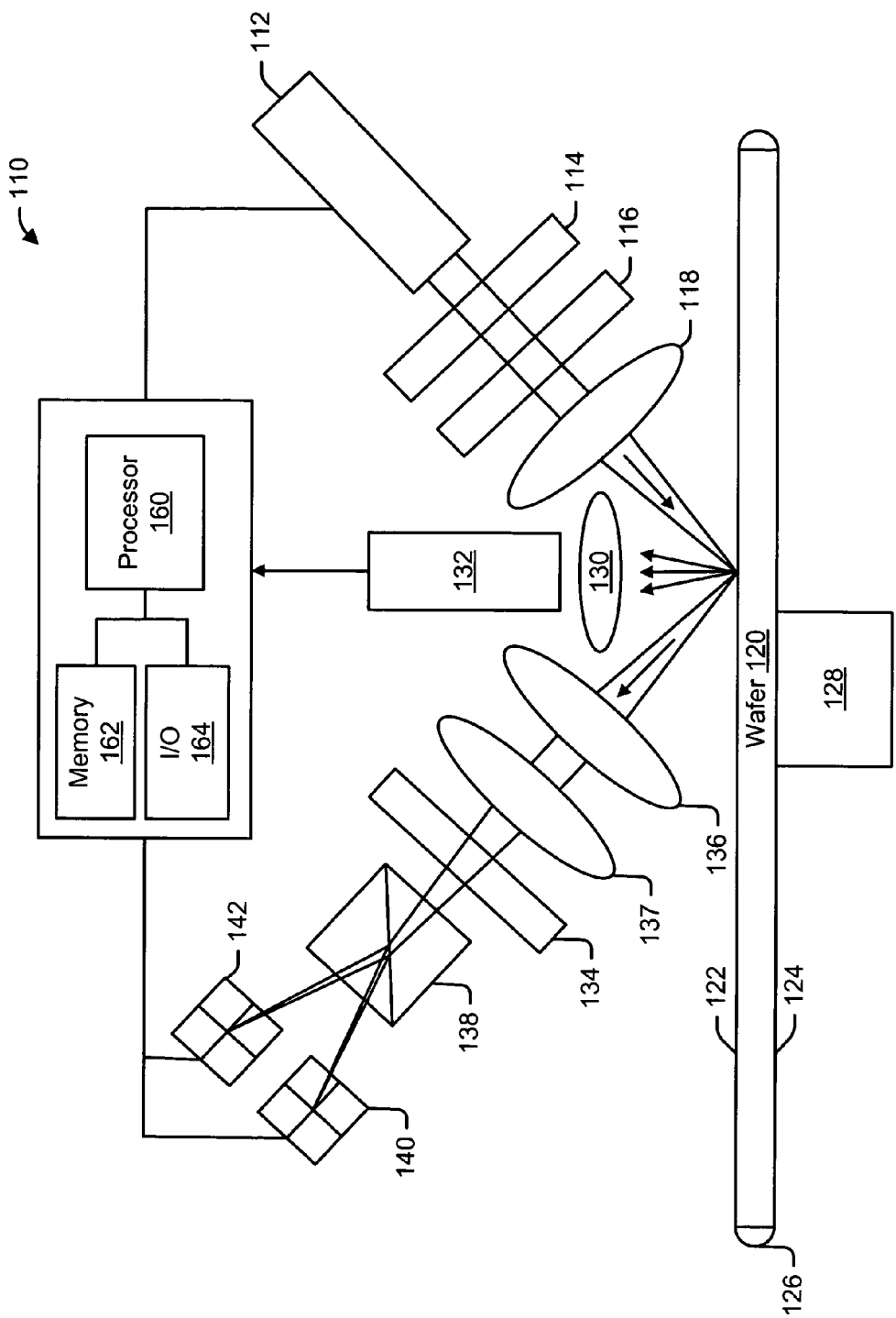
FIG. 1 is a schematic illustration of various optical components of an embodiment of an apparatus for wafer surface and edge inspection.

FIG. 1 is a schematic illustration of one embodiment of an apparatus for wafer surface inspection. Various optical testing components and techniques for surface inspection are described in U.S. Pat. Nos. 6,665,078, 6,717,671, and 6,757,056,and 6,909,500 to Meeks, et al., the disclosures of which are incorporated herein by reference in their entirety. Any of the assemblies and techniques described in these patents may be used in a surface analyzer for detecting surface pits.

One embodiment is adapted to perform film thickness measurements, surface roughness measurement, reflectivity measurement, magnetic imaging, and optical profiling using radiation in the optical spectrum. In alternate embodiments radiation outside the optical spectrum may be used. More particularly, FIG. 1 depicts an optics assembly capable of performing the above mentioned measurements that includes a combined reflectometer, scatterometer, phase shift microscope, magneto-optic Kerr effect microscope and optical profilometer. This embodiment is capable of detecting and classifying a wide variety of defects on a wafer or disk surface or edge or near edge.

Wafer 120 includes an upper surface 122, a lower surface 124, and an edge surface 126, which may be substantially flat or curved when viewed in a cross-sectional profile. In the embodiment depicted in FIG. 1, the wafer edge surface is curved when viewed in cross-sectional profile.

A surface analyzer assembly 110 is positioned to direct radiation onto a surface of wafer 120. In the embodiment depicted in FIG. 1, surface analyzer assembly 110 includes a laser diode 112, an optional polarizer 114, an optional half-wave plate 116, and a focusing lens 118 for directing radiation onto a surface of wafer 120. These components target radiation from the laser diode onto the surface of wafer 120, and hence may be considered a radiation targeting assembly. In alternative embodiment polarizer 114 and half-wave plate 116 may be omitted.

Surface analyzer assembly 110 further includes a collecting lens 130 and a photomultiplier tube (PMT) 132. These components collect radiation scattered by the surface of the wafer 120, and hence may be considered a scattered radiation assembly. In alternative embodiments the PMT 132 and collecting lens 130 may be replaced with an integrating sphere or an ellipsoidal mirror together with a PIN photodiode or avalanche photodiode.

Surface analyzer assembly 110 further includes a collimating lens 136, an optional wobble reduction lens 137, a quarter wave plate 134, a Wollaston prism 138 rotated at 45 degrees to the plane of incidence, and two quadrant detectors 140, 142 available from Hamamatsu, Inc. In another embodiment, detectors 140 and 142 may be PIN photodetectors also available from Hamamatsu, Inc. The embodiment shown in FIG. 1 utilizes quadrant detectors so that the slope of the surface may be measured. The surface slope may be integrated to produce the surface profile. These components collect radiation reflected from the surface of wafer 120, and hence may be considered a reflected radiation assembly. The optional wobble reduction lens 137 is a converging lens. In alternative embodiments the wobble reduction lens 137 and the collimating lens 136 may be combined into a single lens. The optional wobble reduction lens is chosen so that its focal length is substantially equal to the distance between wobble reduction lens 137 and the quadrant detectors 140 and 142. When this is done the surface slope measured at the quadrant detectors will be minimized. That is, the system will be most tolerant of wobble of the wafer. Another embodiment would position the detectors 140 and 142 at a distance slightly longer or shorter than the focal length of the wobble reduction lens 137. In this case the system would have some sensitivity to both wafer wobble and to surface slope.

In one embodiment surface analyzer assembly 110 uses a multi-mode, multi-wavelength laser diode 112 which is available from Rohm Co., LTD Kyoto, Japan as model number RLD-78MV and a polarizer 114 which is adjusted for P polarization and improves the extinction ratio of the laser. The radiation may be of any wavelength. In one embodiment a 405 nm violet source available from Coherent, Inc may be implemented. In another embodiment a 635 nm source may be implemented. The mechanically rotatable half wave plate 116 is available from CVI Laser Corp. and can be used to rotate the polarization between 45 degree rotated linear polarization, and P or S polarization. Alternative techniques for rotating the polarization include: rotating the laser diode 112 or to use a liquid crystal polarization rotator such as model LPR-100 available from Meadowlark Optics, Frederick, CO. The latter embodiment has the advantage of being a purely electronic means of polarization rotation and as a result there is no possibility of beam movement when the polarization is rotated.

Focusing lens 118 creates a small spot on the surface of a wafer 120. The PMT 132 and collecting lens 130 are used to measure the scattered light for the purposes of computing the surface roughness, detecting micro-pits, measuring debris or particles, detecting stains, cracks, scratches, delaminations, blisters or corrosion on the disk or wafer 120 surface or edge 126 or near edge regions.

After reflecting from the disk, the beam passes through the collimating lens 136, the optional wobble reduction lens 137, and a quarter-wave plate 134. The beam is then polarization split with a Wollaston prism 138 available from CVI Laser Corp., for example, and each polarization component is detected with separate photodetectors 140, 142. The plane of the Wollaston prism (the plane of the S and P components) may be adjusted at substantially 45 degrees to the plane of incidence. The first mixed component of the beam (which includes both P and S components with respect to the plane of incidence) is directed to a detector 140 and the second mixed component (which includes both P and S components with respect to the plane of incidence) is directed to a second detector 142. In one embodiment the photodetectors 140, 142 may have a diffuser placed in front of them to reduce the residual position sensitivity of the photodiodes. The difference between the intensity measured by the photodetectors is proportional to the cosine of the phase difference between the first and second mixed components coming from the Wollaston prism. As a result this instrument can get different types of information when used in different modes.

When the polarization is adjusted to P, the P specular and P scattered light is measured resulting in sensitive measurements of carbon thickness (or any simple layer thickness) and carbon wear. The P specular signal is obtained by rotating the half wave plate 116 so that the polarization output from the half wave plate is P polarized. The P specular signal is given by the sum of the signal from 140 and 142. When the polarization is adjusted to 45 degrees (exactly between P and S polarization) the instrument is most sensitive to measurements of the phase change induced by changes in the thickness of the thin films on the disk or wafer surface. In the phase shift mode the instrument measures lubricant, carbon, or other film thickness changes on thin film disks or wafers. The phase shift is measured by taking the difference between the signals measured at 142 and 140. This gives an output that is proportional to the cosine of the phase difference between the first and second mixed components of the wave. The orientation of the quarter wave plate 134 is adjusted to optimize the sensitivity to lubricant, carbon wear, other film thickness changes or changes in phase due to the presence of defects. The individual components may also be measured; that is, the first and second mixed components of the 45 degrees polarized light. These are measured simultaneously with the phase shift and the scattered light.

When the half wave plate is rotated so that the polarization is adjusted to S polarization the instrument will be able to measure the S specular and the S scattered light and, as a result, obtain the surface roughness and other properties of the sample. The S specular signal is given by the sum of the signal from 140 and 142. The angle of incidence shown in FIG. 1 is 58 degrees but angles greater or less than 58 degrees will work as well. The longitudinal Kerr effect can be measured by operating the instrument in any of the linear polarization's, i.e., P, S or 45 degrees. Rotating the quarter wave plate 134 to achieve maximum sensitivity to the magnetic pattern optimizes the Kerr effect signal. The orientation of the quarter wave plate which optimizes the Kerr effect may be different from that which optimizes for lubricant and carbon sensitivity. As a result the quarter wave plate is made to be removable, for example, so that two different and separately optimized plates can be used for the different applications. A different embodiment would have a miniature motor to rotate the orientation of the quarter wave plate so as to optimize the signal for the Kerr effect, lubricant, carbon or defect detection mode. Different polarizations may require a different quarter wave plate adjustment to achieve optimization. When in this mode the instrument functions as a Kerr effect microscope. In one embodiment the S polarization is used to image the longitudinal Kerr effect. When the surface is imaged by the OSA in S linear polarization the reflected light has its polarization converted to elliptical polarization whose major axis is rotated depending upon the orientation of the magnetization upon the thin film disk. This Kerr effect signal is detected by measuring the two signals coming from the polarization beam splitter and subtracting them. This will give a signal whose sign is related to the direction of the magnetization and whose amplitude is proportion to the magnetization.

The data collected by the scattered radiation collection assembly and the reflected radiation collection assembly is fed to a processing module that includes a processor 160, a memory module 162, and an I/O module 164. Processor module comprises logic instructions that enable the instrument described in FIG. 1 to simultaneously measure the profile (height and depth) of the surface, the S and P components of the reflectivity, the phase shift between the P and S waves and the scattered light. It is also capable of measuring the Magneto-optic Kerr effect.

The measurement of the phase shift between the S and P components of the optical wave requires a means to stabilize the long-term phase drift of the diode laser. This can be accomplished by the use of a reference mirror. The reference mirror is a stable surface such as a gold mirror, a section of a thin film disk, or section of a silicon wafer. The reference mirror is calibrated when the instrument is first set up by measuring and recording the phase shift of the reference mirror. At times after the initial calibration of the instrument the reference mirror is measured prior to a measurement of the sample. Any deviation of the reference mirror reading from the initial reading is recorded and subtracted from the measurement of the sample readings. This insures that the phase shift reading from the surface under measurement will remain stable over time. The same procedure can also be applied to the measurement of the S specular and P specular signals. In this case when the instrument is calibrated the values of the P specular and S specular signals measured on the reference mirror are recorded and deviations from these values are used to correct the specular data. This removes any drift from the P and S specular signals.

The above discussion is relating to an instrument, which has an angle of incidence that is near 60 degrees from the vertical. Similar ideas can be applied to a machine operating at angles less than or greater than 60 degrees. When the angle of incidence changes the interpretation of the various quadrants of the histogram will change.

Figure 2:
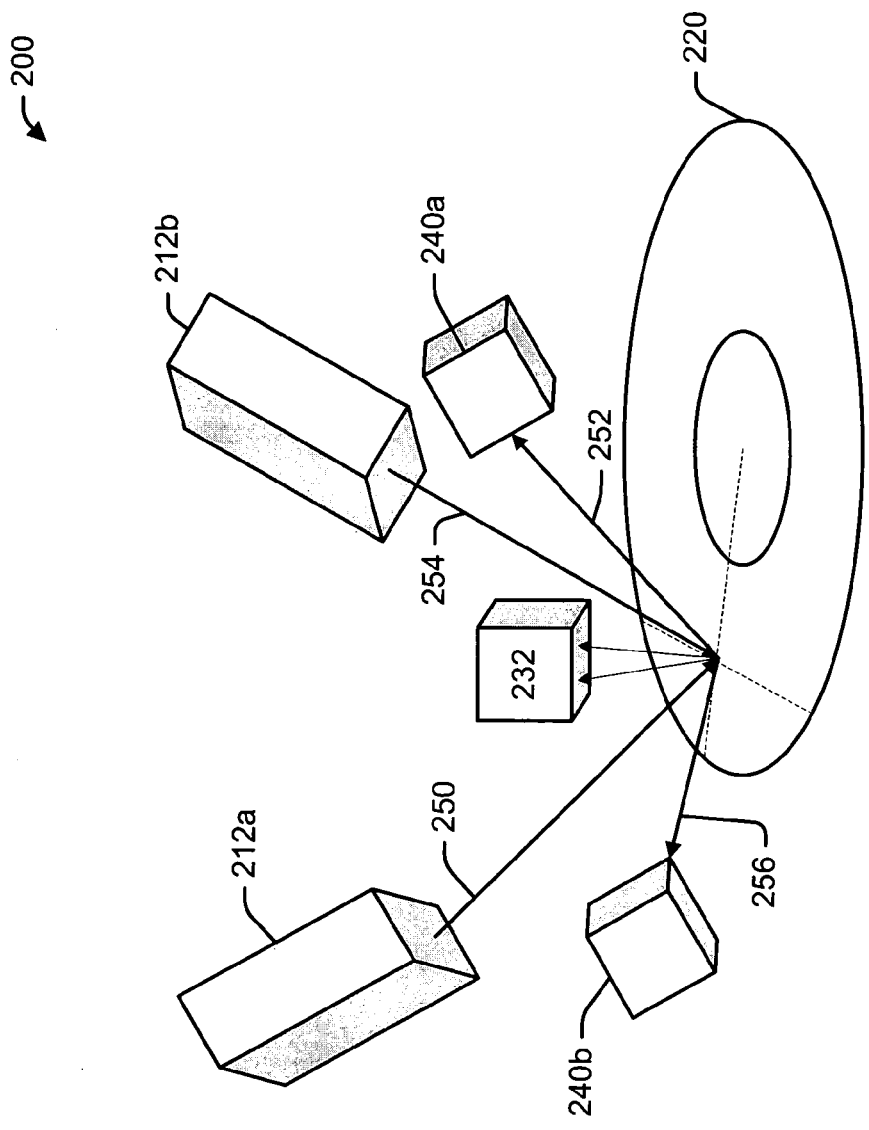
FIG. 2 is a schematic illustration of one embodiment of an apparatus for wafer surface and edge inspection.

FIG. 2 is a schematic illustration of one embodiment of a system 200 adapted to detect surface pits on a substrate such as, for example, a wafer 220. In one embodiment, wafer 220 may be mounted on a spindle and rotated about a central axis, as illustrated in FIG. 1. Referring briefly to FIG. 2, system 200 includes a first radiation directing assembly 212a that directs a first radiation ray 250 onto the surface of wafer 220 and a second radiation directing assembly 212b that directs a second radiation ray 254 onto the surface of wafer 220. System 200 further comprises a first collecting assembly 232 that collects radiation scattered from the surface of wafer 220.

In one embodiment, system 200 may include a second collecting assembly 240b that collects a portion of the radiation ray 256 reflected from the surface of wafer 220 and a third collecting assembly 240a that collects a portion of the radiation ray 252 reflected from the surface of the wafer 220.

In one embodiment each of the radiation directing assemblies 212a, 212b may include some or all of the components 112, 114, 116, 118 described in the embodiment depicted in FIG. 1. Similarly, the collecting assemblies 240a, 240b may include some or all of the components 136, 137, 134, 138, 140, 142. The collecting assembly 242 may include some or all of the components 130, 132. The system 200 may be coupled to a processing device such as the processing device 160, 162, 164 depicted in FIG. 1.

Figure 3:
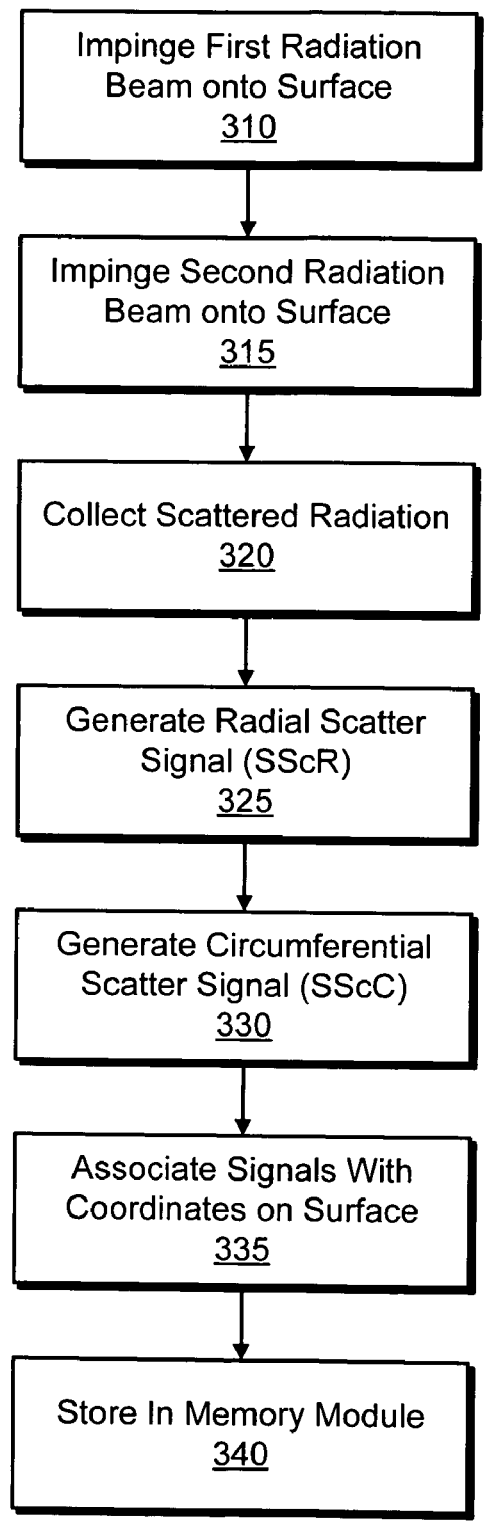
FIG. 3 is a flowchart illustrating operations in a method for detecting surface pits.

FIG. 3 is a flowchart illustrating operations in a method for detecting surface pits. At operation 310 a first radiation beam is directed onto the surface of wafer 220, and at operation 315 a second radiation beam is directed onto the surface of wafer 220.

In one embodiment, the first radiation directing assembly 212a may be oriented such that the radiation ray 252 impinges the surface of the wafer 220 approximately along a radial axis of the surface. The second radiation directing assembly 212b may be oriented such that the radiation ray 254 impinges the surface of wafer 220 along an axis that is substantially orthogonal to the radial axis, referred to herein as a circumferential axis. These axes are illustrated by dashed lines on the surface of wafer 220. In alternate embodiments the two axes need not be orthogonal. In alternate embodiments the two axes may be aligned along axes that are neither precisely radial nor circumferential.

The radiation beams 250, 254 are scanned across the surface of the wafer 220. In one embodiment, the wafer 220 may be rotated about a central axis, e.g., by spinning the wafer on a spindle, and the optical components may be translated along a radial axis, such that the entire surface of wafer 220 is scanned. In alternate embodiments, the wafer may remain stationary and the components may be moved across the surface of wafer 220. Alternatively, the spinning wafer may be translated in the radial direction beneath the stationary optical components.

In one embodiment, radiation directing assemblies 212a, 212b are adapted to direct S-polarized light onto the surface of wafer 220 at a wavelength of 780, 532, 655, 405 or 375 nanometers. In general, any laser wavelength may be used. In an alternate embodiment, radiation directing assemblies are adapted to direct both S-polarized light and P-polarized light onto the surface of wafer 220. This may be accomplished, e.g., by including a rotatable half-wave plate to alternate between S-polarization and P-polarization.

At operation 320 radiation scattered from the surface of wafer 220 is collected. In operation, radiation collecting assembly 232 collects a portion of the radiation scattered from the surface of wafer 220. Similarly, radiation collecting assembly 240a collects a portion of the radiation from the first light directing assembly 212a reflected from the surface of wafer 220. Similarly, radiation collecting assembly 240b collects a portion of the radiation from the second light directing assembly 212b reflected from the surface of wafer 220.

The radiation collecting assemblies 232, 240a, 240b generate signals representative of characteristics of the radiation received. At operation 325 the radiation collecting assembly 232 generates a signal representative of the scatter in the S-polarized radiation from radiation directing assembly 212a, referred to herein as the radial scatter signal (SScR). At operation 330 the radiation collecting assembly generates a signal representative of the scatter in the S-polarized radiation from radiation directing assembly 212b, referred to herein as the circumferential scatter signal (SScC).

At operation 335 the signals SScR and SScC are associated with coordinates on the surface of wafer 220. In one embodiment, the surface of wafer 220 may be mapped in (x, y) coordinates. In an alternate embodiment, the surface of wafer may be mapped in radial coordinates or any other suitable coordinate system. At operation 335 the signals SScR and SScC and the associated coordinates are stored in a memory module such as, e.g., the memory module 162 depicted in FIG. 1.

Figure 4:
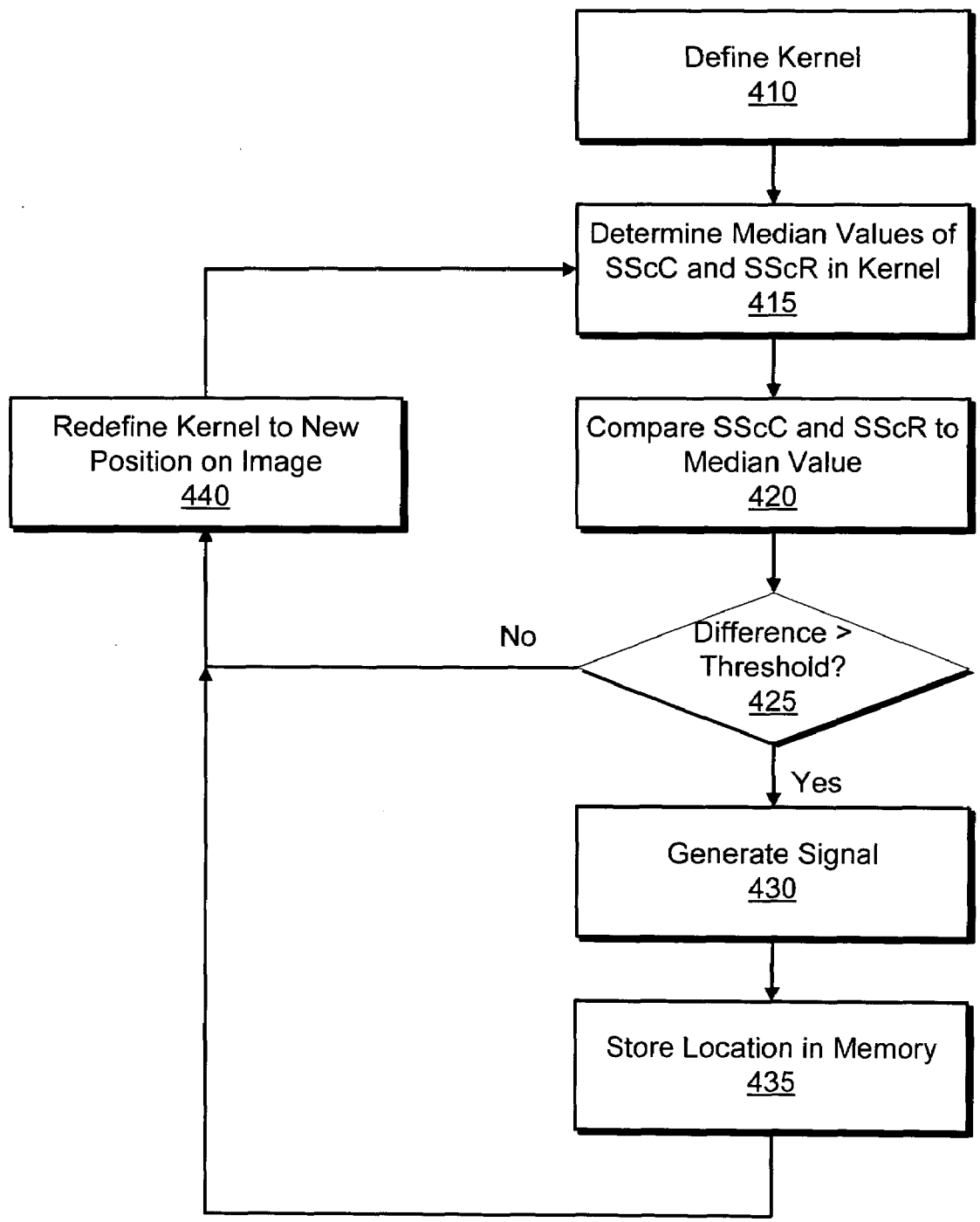
FIG. 4 is a flowchart illustrating operations in a method for detecting surface pits.

The signal values recorded in memory in operation 335 may be used to detect pits in the surface of wafer 220. FIG. 4 is a flowchart illustrating operations in a method for detecting surface pits. In one embodiment, the operations illustrated in FIG. 4 may be implemented as logic instructions stored in a computer-readable medium such as, e.g., the memory module 162 depicted in FIG. 1. At operation 410, a kernel is defined. As used herein, the term "kernel" refers to an array of signal values and coordinate data collected using the operations of FIG. 3. For example, kernel may represent the values of SScC and SScR recorded over a section of the surface of wafer 220. In one embodiment, the kernel may represent a moving window of SScC and SScR recorded over a length range between 300 micrometers and 3000 micrometers. In general, the shape of the kernel may be linear, square or any two-dimensional shape.

At operation 415 median values of SScC and SScR are determined using the data points recorded in the kernel defined in operation 410. In an alternate embodiment average values may be determined.

At operation 420 the values of SScC and SScR recorded at discreet data points in the kernel are compared to the median value of SScC and SScR for the kernel determined in operation 415. If, at operation 425, the difference between the value of SScC and the median value of SScC calculated in operation 415 or the difference between the value of SScR and the median value of SScR calculated in operation 415 exceeds a threshold, then control passes to operation 430 and a signal is generated. The signal indicates that a surface defect that may be a surface pit is located at the coordinates of the data point being compared with the median value of SScC and SScR. In one embodiment, the signal may be associated with the coordinates in a memory module such as, for example, the memory module 162 depicted in FIG. 1.

By contrast, if at operation 425 the difference is less than a threshold, then control passes to operation 440 and the kernel is redefined to cover a new position on the image of the scanned surface. Control then passes back to operation 415 and new median values are calculated for the kernel. This process is repeated until the entire disk or wafer (or a portion thereof) has been examined for defects such as pits, scratches, particles or other types of defects.

In one embodiment the threshold may be static and may represent a factor of the median value calculated in operation 415. For example, the threshold may be set to a factor of 150% or 200% of the median value. In an alternate embodiment the threshold may be dynamic.

In an alternate embodiment, the median (or average) values of SScC and SScR may be subtracted from the values of SScC and SScR recorded at specific locations on the surface of wafer 220, and the result may be compared to a threshold. Subtracting the median values of SScC and SScR effectively compensates for the median or average surface noise in the kernel. The noise-compensated signal may be compared to a threshold.

In an alternate embodiment, a noise-compensation signal may be created by subtracting a signal generated by P-polarized light from the second radiation directing assembly 212b scattered from surface of wafer 220, referred to herein as the PScC signal, from the SScC signal. In one embodiment, the PScC signal may be scaled by a suitable scaling factor (typically between 0.5 and 1.5). Further, the PScC signal may be first median filtered and then subtracted from the SScC signal. This will remove the background noise signal from the SScC signal and leave the signal from pits.

In an alternate embodiment, a noise-compensation signal may be created by subtracting a signal generated by P-polarized light from the first radiation directing assembly 212a scattered from surface of wafer 220, referred to herein as the PScR signal from the SScR signal. In one embodiment, the PScR signal may be scaled by a suitable scaling factor (typically between 0.5 and 1.5). Further, the PScR signal may be first median filtered and then subtracted from the SScR signal. This will remove the background noise signal from the SScR signal and leave the signal from pits.

In an alternate embodiment, the SScR and SScC signals may be summed to produce a signal with increased signal and decreased background noise.

In alternate embodiments, the system 200 may be used to distinguish pits in the surface of wafer 200 from particles or other imperfections on the surface of wafer 200. Particles on the surface of wafer 200 generate strong negative signals from the detectors 240a, 240b that detect specularly reflected light. By contrast, pits generate weak negative signals from the detectors 240a, 240b that detect specularly reflected light.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system to detect pits in a surface, comprising:
    a first radiation targeting assembly to target a first radiation beam onto a surface;
    a second radiation targeting assembly to target a second radiation beam onto a surface;
    a first radiation collecting assembly that collects radiation scattered from the surface;
    a processor coupled to the first radiation collecting assembly;
    a memory module coupled to the processor and comprising logic instructions which, when executed by the processor, configure the processor to:
    generate a first signal from radiation scattered from the first radiation beam;
    generate a second signal from radiation scattered from the second radiation beam;
    record the first signal and the second signal at an array of different positions on the surface;
    calculate a median value for the first signal and the second signal over the array of different positions on the surface; and
    use the first signal, the second signal, and the median value to detect pits in the surface.

2. The system of claim 1, wherein:
    the first radiation directing assembly directs a radiation beam along a radial axis; and
    the second radiation directing assembly directs a radiation beam along a circumferential axis.

3. The system of claim 1, wherein the first radiation beam and the second radiation beam are directed along orthogonal axes.

4. The system of claim 1, further comprising a second radiation collecting assembly.

5. The system of claim 1, wherein the memory module further comprises logic instructions which, when executed by the processor, cause the processor to compare first and second signals at a point on the surface with a noise-compensated signal at the point on the surface.

6. A method to detect pits in a surface, comprising:
    scanning a first radiation beam across portions of a surface, wherein the first radiation beam impinges the surface along a first axis;

scanning a second radiation beam across portions of the surface, wherein the second radiation beam impinges the surface along a second axis substantially orthogonal to the first axis;

generating a first signal value from radiation scattered from the first radiation beam;

generating a second signal value from radiation scattered from the second radiation beam;

recording the first signal value and the second signal value at an array of different positions on the surface;

calculating a first median value for the first signal value and a second median value for the second signal value over the array of different positions on the surface; and using the first signal, the second signal, and the median value to detect pits in the surface.

7. The method of claim 6, wherein:
the first radiation beam comprises S-polarized light; and
the second radiation beam comprises S-polarized light.

8. The method of claim 6, wherein the array of different positions on the surface represents a two-dimensional area on the surface.

9. The method of claim 6 wherein the array of different positions on the surface represents a one-dimensional area on the surface.

10. The method of claim 6, wherein the median value represents an average noise signal over the array of different positions on the surface.

11. The method of claim 6, wherein using the first signal, the second signal, and the median value to detect pits in the surface comprises comparing the first signal value and the second signal value to the median signal value.

12. The method of claim 6, wherein using the first signal, the second signal, and the median value to detect pits in the surface comprises:

subtracting the first median value from the first signal value to obtain a first noise-compensated signal value; and comparing the first noise-compensated signal value to a threshold.

13. The method of claim 6, wherein using the first signal, the second signal, and the median value to detect pits in the surface comprises:

subtracting the second median value from the second signal value to obtain a second noise-compensated signal value; and comparing the second noise-compensated signal value to a threshold.

14. The method of claim 6, wherein:
the first radiation beam comprises P-polarized light and S-polarized light; and
the second radiation beam comprises P-polarized light and S-polarized light.

15. The method of claim 14, further comprising:
subtracting a signal generated from the P-polarized light scattered from the surface from a signal generated from the scattered S-polarized light scattered from the surface.

16. A system to detect pits in a surface, comprising:
a radiation targeting assembly to target a first radiation beam onto a surface along a first axis and a second radiation beam onto the surface along a second axis, different from the first axis;

a first radiation collecting assembly that collects radiation scattered from the surface;

a processor coupled to the first radiation collecting assembly;

a memory module coupled to the processor and comprising logic instructions which, when executed by the processor, configure the processor to:

record signal values from radiation scattered by the first radiation beam and the second radiation beam at different positions on the surface;

generate a noise-compensated signal form the signal values; and use the signal values and the noise-compensated signal to detect pits in the surface.

17. The system of claim 16, wherein:
the radiation beam is targeted along a radial axis; and
the second radiation beam is targeted along a circumferential axis.

18. The system of claim 16, wherein the first radiation beam and the second radiation beam are directed along orthogonal axes.

19. The system of claim 16, further comprising a second radiation collecting assembly.

20. The system of claim 16, wherein the memory module further comprises logic instructions which, when executed by the processor, cause the processor to compare the signal values at a point on the surface with a noise-compensated signal at the point on the surface.

* * * * *